United States Patent [19]

Lee et al.

[11] 4,248,380
[45] Feb. 3, 1981

[54] AQUEOUS-BASED AIR TREATING SYSTEMS

[75] Inventors: Ping I. Lee, Ossining; Eduard K. Kleiner, New York, both of N.Y.

[73] Assignee: Airwick Industries, Inc., Carlstadt, N.J.

[21] Appl. No.: 864,980

[22] Filed: Dec. 27, 1977

[51] Int. Cl.³ .............................................. A61L 9/04
[52] U.S. Cl. ........................................ 239/6; 239/53
[58] Field of Search ............. 239/6, 34, 43, 44, 54-60

[56] References Cited

U.S. PATENT DOCUMENTS

| | | | |
|---|---|---|---|
| 3,567,118 | 3/1971 | Shepherd | 239/53 X |
| 3,578,545 | 5/1971 | Carson et al. | 239/56 |
| 3,596,833 | 8/1971 | Gould | 239/54 |
| 3,685,734 | 8/1972 | Paciorek et al. | 239/56 |
| 3,688,985 | 9/1972 | Engel | 239/54 |
| 3,815,828 | 6/1974 | Engel | 239/6 |
| 3,885,737 | 5/1975 | Watkins | 239/55 X |
| 3,985,298 | 10/1976 | Nichols | 239/54 |
| 4,017,030 | 4/1977 | Coplan et al. | 239/53 |
| 4,094,119 | 6/1978 | Sullivan | 239/56 X |
| 4,130,245 | 12/1978 | Bryson | 239/56 |

FOREIGN PATENT DOCUMENTS 1325227 8/1973 United Kingdom ................ 239/6 UX Primary Examiner—Robert B. Reeves
Assistant Examiner—Gene A. Church
Attorney, Agent, or Firm—Harry Falber

[57] ABSTRACT

A system for the controlled release of air treating material comprising a hydrophilic membrane secured to a reservoir containing an active ingredient in aqueous medium, the membrane serving as the means for releasing the active ingredient to the atmosphere and for controlling the rate of release.

13 Claims, 7 Drawing Figures

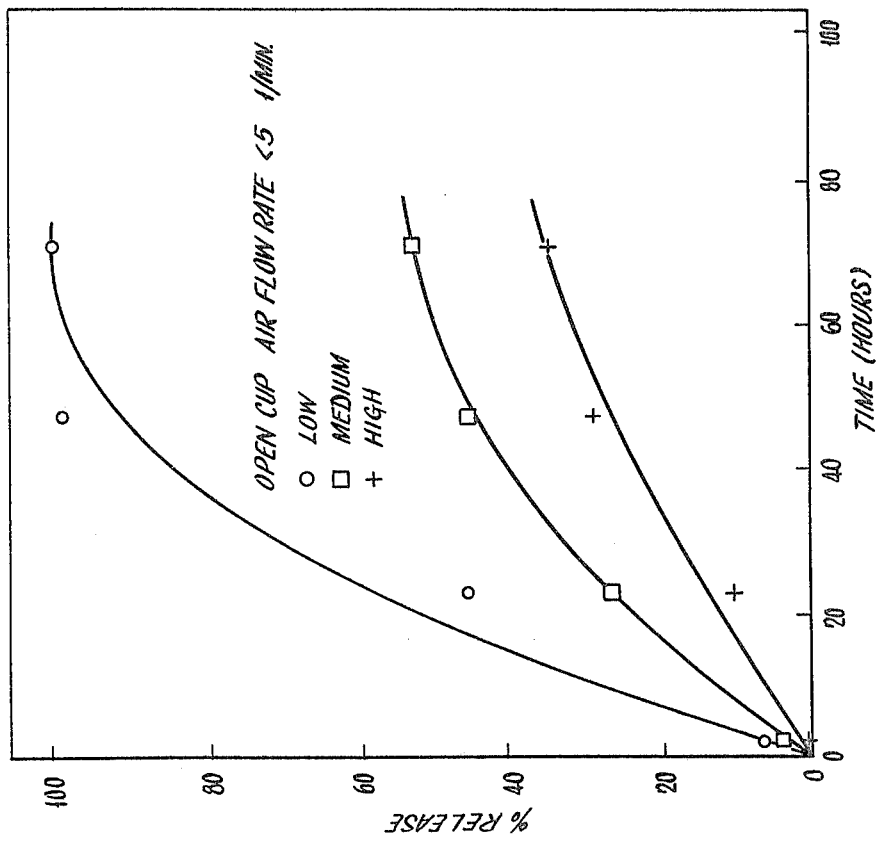
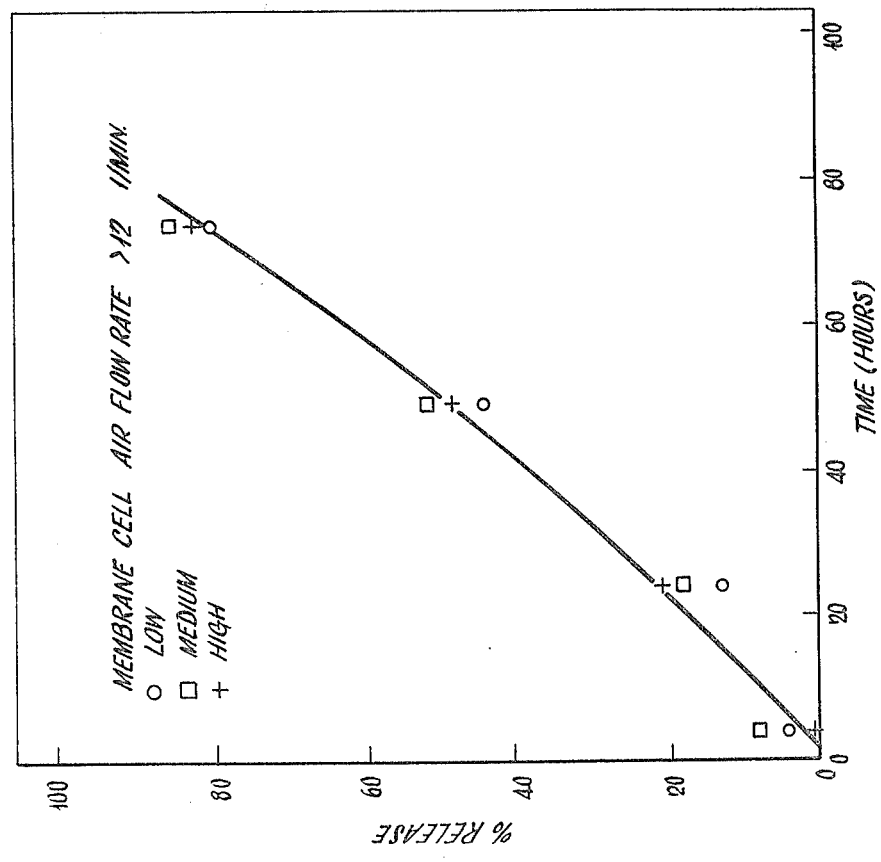

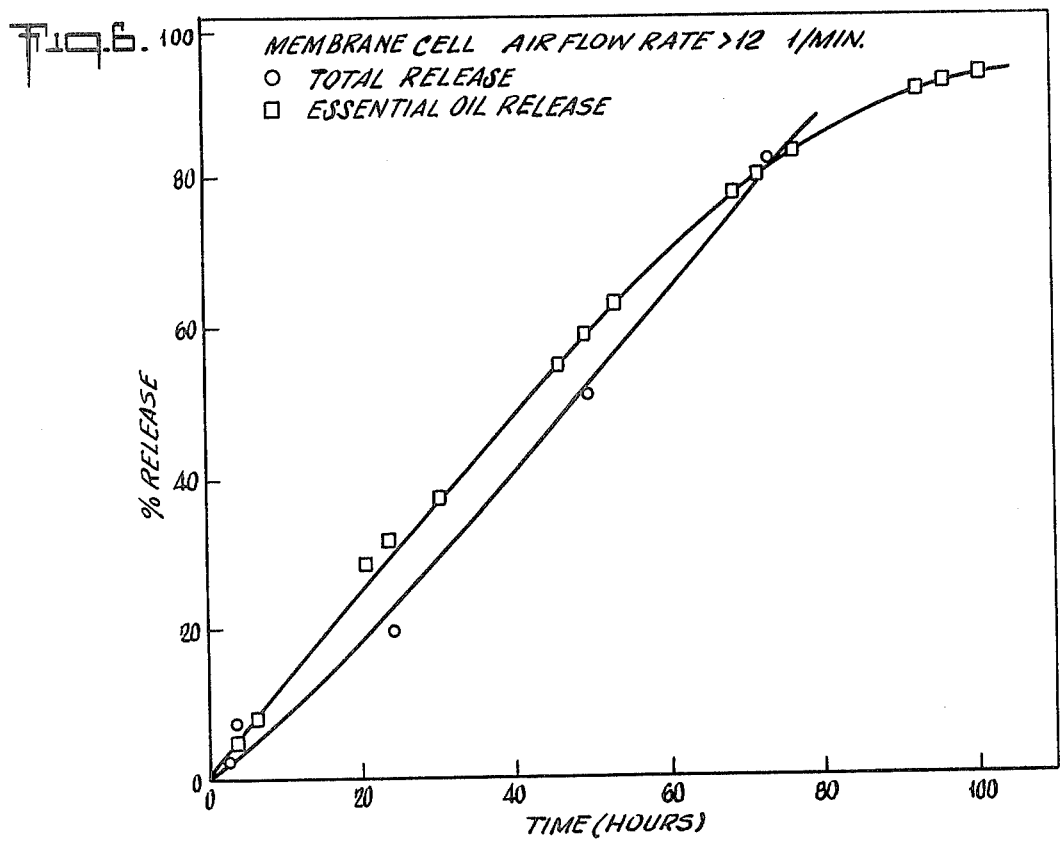
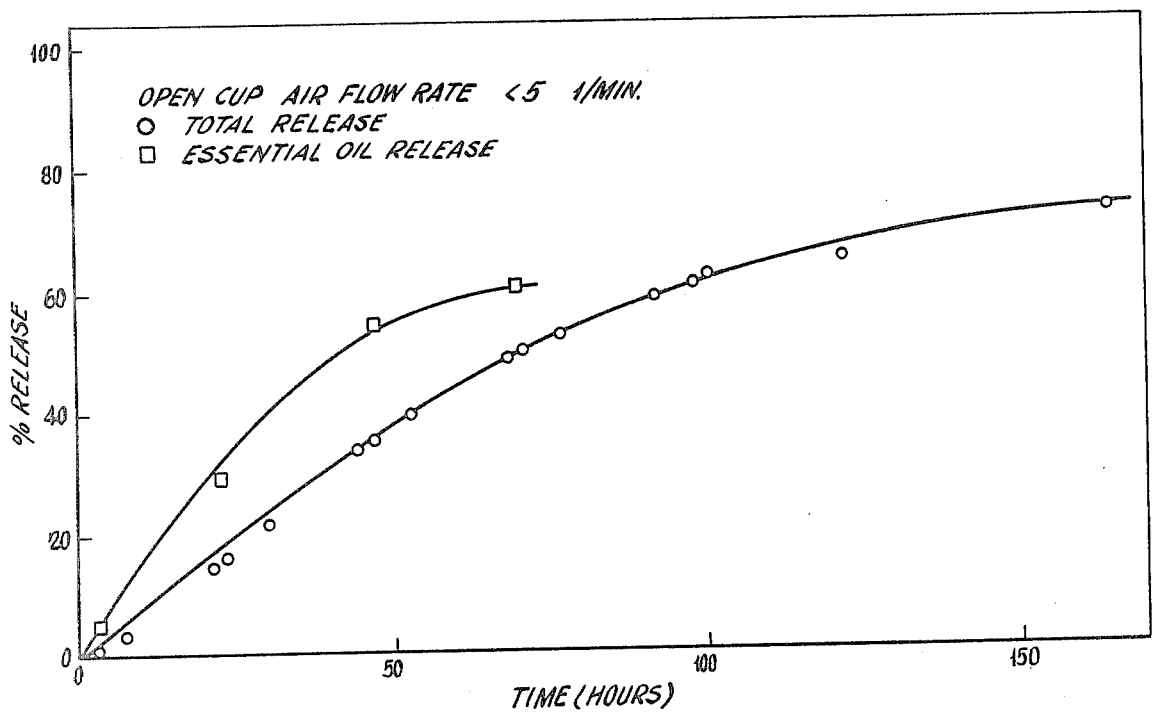

AQUEOUS-BASED AIR TREATING SYSTEMS

The sale and manufacture of air-treating agents, and in particular room deodorizers and the like, has expanded substantially with the result that a variety of air-treating products or agents have been developed for commercialization. Predominant among these are the liquid-wick types and the solid air-treating agents, i.e. solid compositions from which volatile air-treating materials slowly vaporize when the solid is exposed to air. Certain of such air-treating agents, described in U.S. Pat. Nos. 2,691,615 and 2,929,055, comprise a solid gel containing volatile air-treating materials.

Air-treating agents of this type have many advantages and have been found to be highly satisfactory in use. However, these systems generally exhibit a less-than-desirable release mode. Thus, their rate of release of active ingredient is initially high which is then followed by a rapid decline with the passage of time. Such a pattern of exponential decay may be referred to as "first-order decay". As a result, the amount of released agent may initially exceed the amount required for effective air treatment, while at some later time it may be inadequate for the task. Furthermore, the release rates of such systems will be affected by temperature and humidity changes, thereby introducing additional variables that must be considered by the practitioner skilled in the art. In addition, fractionation of the components of the essential oil concentration is seen to occur thereby further increasing the possibility of erratic release patterns. Thus, the pleasant fragrance that may initially be present will vary and disappear with the passage of time and with the resultant change in concentration of the various essential oil components. Correspondingly, the effective odor counteraction that may be achieved initially will also vary and diminish with time. These effects are seen to occur as the lower boiling component concentration diminishes in favor of that of the higher boiling components.

Various systems which are seen to exhibit such "first-order" decay are disclosed in U.S. Pat. Nos. 3,400,890; 3,596,833; 3,567,118; 2,481,296; and 3,578,545. The element common to each of these systems is that the active ingredient is homogeneously dispersed or dissolved through the basic matrix. This matrix can be as thin as a membrane (U.S. Pat. No. 3,567,118) or as thick as a chunk of gel. The kinetics of release from such a matrix depend greatly on the geometry and loading of the system. As noted above, these systems exhibit exponential decay of release rate with respect to time. Gradually diminishing and varying fragrance level and odor counteraction are observed rather than the desired constant, uniform, controlled release of fragrance.

It is, therefore, the prime object of this invention to provide a system for delivery of air-treating agents which provides a substantially uniform, controlled release of said agents to the atmosphere.

It is a further object to provide a system which avoids an initial high rate of release in favor of a "zero-order" release.

It is still a further object to provide a system which substantially minimizes fractionation among the components of the essential oils as well as between the water and essential oil ingredients.

It is another object to provide a suitable container for the above-noted system.

Various other objects and advantages of this invention will become apparent from the following description thereof.

We have now discovered that by preparing a reservoir device containing a hydrophilic membrane in contact with the active ingredient which is present in an aqueous medium, release of air-treating material can be achieved according to a "zero-order" pattern. In this manner, the liquid mixture is in direct contact with one side of the membrane and the permeated product is removed from the other side. The procedure basically involves selective sorption of active material and water into the membrane, selective diffusion or flow through the membrane and then desorption into the air.

Thus, by utilizing hydrophilic membranes in reservoir devices, constant release of the aqueous-based air-treating material is attained. The presence of the water is essential in that it plasticizes the membrane and lowers the glass transition temperature of the membrane material such that the diffusive transport rate of active material through the membrane can be of practical value. The hydrophilic membrane then meters the transport of aqueous-based active ingredient from the enclosed reservoir at a constant rate for a prolonged and controllable period of time. This is in contrast to the prior art systems which, as previously noted, exhibit a gradually diminishing level of active ingredient. Furthermore, the kinetics of release do not depend on the geometry and loading of the system. Rather, the total period of release depends solely on the reservoir size.

In addition, the controlled release of aqueous-based air treating agent by the use of a hydrophilic membrane exhibits minimal amounts of fractionation among the essential oil components. Thus, contrary to conventional wick systems, for example, which exhibit fast release of the low boiling components followed by the medium and high boilers, the instant systems exhibit similar percentage releases for all three portions. This significant absence of fractionation may be attributed to the closeness of the permeabilities of the fractions through the swollen hydrophilic membrane. Despite the large differences in boiling point, the permeabilities of these components through the membrane generally vary less than one order of magnitude. This, in turn, gives rise to the closeness of the percentage releases of the essential oil components. In other words, it is no longer the evaporation process that is the rate-controlling step but, rather, the permeation through the membrane. As a result, there is a uniformity of fragrance throughout the entire period of activity. The initial, desired fragrance is substantially maintained without the variation resulting from component fractionation. Likewise, the desired and expected level of odor counteraction is maintained without the diminution resulting from component fractionation.

It is also possible to achieve limited fractionation between the water and essential oil as a result of proper formulation of the system. Thus, undesirable release modes wherein only a portion of the essential oil is released before the water content is depleted or wherein the essential oils release and deplete faster than water are avoided. Accordingly, the unnecessary waste of essential oil and possible insufficient release rate of the first mode as well as the initially higher than required release and subsequent diminished fragrance level of the second mode are substantially eliminated. The instant system thus establishes that the release rates of the water and essential oil are proportional to their weight fractions by a similar constant so as to avoid the undesirable release patterns described hereinabove.

We have also developed containers for the novel reservoir systems of this invention. Thus, rigid containers wherein the membrane represents one side thereof as well as collapsible containers can be used. The containers will generally be fitted with means for vacuum relief.

All conventional fragrances, i.e. volatile odorous agents, including essential oils, aromatic chemicals and the like, are applicable for use in the instant systems. A wide variety of such materials are known to those skilled in the perfuming arts. They may comprise one or more natural materials or synthetic aromatic agents or mixtures of the two.

The active ingredients are necessarily present in a water-based system. This may comprise a solution of active ingredients in water or a water-solvent mixture with alcohols, glycols, ketones, aldehydes, and the like, e.g. water-ethanol, water-glycerol, water-ethylene glycol, water-cellosolve, water-acetone, water-acetaldehyde, and the like. Likewise, it may be an emulsion of hydrophobic active ingredients in water or water-solvent mixtures utilizing an appropriate emulsion system. Various optional ingredients may also be included such as surfactants, thickeners, dyes, stabilizers, and the like. The concentration of active ingredient may be selected by the practitioner in accordance with his own particular needs with regard to intensity and duration of fragrance, and the like.

The hydrophilic membrane is selected so as to exhibit good mechanical strength and, most importantly, a minimum equilibrium water content of 15%, and preferably above about 30%. Such values are required in order to maintain effective essential oil permeability. Applicable hydrophilic membranes include cellophane; Cuprophan (cellulosic membrane prepared by cuprammonium process); high molecular weight, fully hydrolyzed polyvinyl alcohol (e.g. manufactured by Mono-Sol Division of Chris-Craft Industries, Inc.); crosslinked polyvinyl alcohol; hydrogels; polyvinyl chloride with inert absorptive filler (e.g. manufactured by Amerace Corp., Butler, N.J.); cellulose triacetate; copolyether polycarbonate; polyethylene glycol-polyethylene terephthalate block copolymer, [see Lyman et al, Biochemistry 3, 985(1964)]; hydrophilic polyurethane (see U.S. Pat. No. 3,822,238); and the like.

Applicable hydrogels are disclosed in numerous references including U.S. Pat. Nos. 3,520,949, 3,632,416, 3,641,237, 3,721,657, 3,784,540, 3,929,741, 3,947,401, and the like. Such hydrogels are polymers of monomers containing at least one hydrophilic group which have been crosslinked with a polyunsaturated crosslinking agent. Such hydrophilic monomers include hydroxyalkyl acrylates and methacrylates, diacetone acrylamide, acrylamide, methacrylamide, acrylamido propane sulfonic acid, 2-(alkoxy) ethyl acrylates and methacrylates, alkyl aminoalkyl methacrylates, ethylenically unsaturated carboxylic acids, vinyl pyrrolidone, diethylene glycol monoacrylate, diethylene glycol monomethacrylate, glyceryl methacrylate, pentaerythritol methacrylate, and the like. Typical crosslinking agents are vinylic, vinylidenic or allylic in nature and include polyunsaturated polyesters formed between a polyhydroxy alcohol and an ethylenically unsaturated carboxylic acid, aliphatic polyvinylic monomers, aromatic polyvinylic monomer, polyalkyl monomers, allyl-vinyl monomers, methacrylic acid anhydride, alpha, omega-diamino acrylamides, and the like. The aforementioned monomers are only exemplary of the large number and variety of hydrogel components known to those skilled in the art which can be utilized in the instant invention.

In addition, the hydrophilic membranes can be further supported by macroporous materials such as woven and nonwoven fabrics, filter paper, cardboard or macroporous plastic materials such as a porous polyvinyl chloride sheet, a porous polypropylene sheet, and the like. In general, any macroporous sheet which does not affect the release kinetics of the hydrophilic membrane system can be used.

With regard to the rate of release, the desired constant rate can be controlled by the type of hydrophilic membrane selected and the membrane thickness and surface area. The total period of release will be determined by the amount of aqueous-based active ingredient. Due to the difference in permeation rate of water and essential oil through any specific water-swollen hydrophilic membrane, it is necessary in the design of a particular unit to consider the amount of essential oil that would be released as long as the membrane is in a water-swollen state. This determination would yield an optimum composition of essential oil in water and thereby eliminate undesired waste or deficiency of active ingredient.

The container adopted to contain the instant system will readily suggest itself to a practitioner skilled in the art. One possibility is a rigid container wherein the membrane serves as one of the walls. The membrane can be supported in any convenient manner. The container should desirably be fitted with means for vacuum relief so as to avoid the formation of a partial vacuum with the passage of time, such means including pinholes, one-way valves, capillary tubes and the like. The container can also be prepared in soft, collapsible form such as a plastic bellow or a plastic packet or envelope. The collapsible construction removes the necessity for including vacuum relief means.

Although the previous discussion has made primary reference to fragrances as the air-treating material, it should be noted that the instant invention is equally applicable to the dispensing of disinfectants, insecticides, respiratory medicines, and the like.

The following examples will further illustrate the embodiment of this invention. In these examples, all parts given are by weight unless otherwise noted.

Some of the results of these experimental examples are described in greater detail with reference to the accompanying drawings wherein:

FIGS. 4–5 are graphical depictions of release (%) versus time (hours) for the various essential oil fractions of the fragrance in membrane cell and open cup environments; and FIGS. 6–7 are graphical depictions of release (%) versus time (hours) of total release and essential oil release in membrane cell and open cup environments.

EXAMPLE I

This example illustrates a typical system of the instant invention.

For purposes of this example, the following hydrophilic membranes were utilized:

| # | Membrane | Thickness (Mils) | Degree of Swelling (%) | Equilibrium Water Content (%) |
|---|---|---|---|---|
| 1 | Hydroxyethyl methacrylate hydrogel | 6.8 | 35.6 | 26.3 |
| 2 | Hydroxyethylmethacrylate hydrogel | 8.0 | 35.6 | 26.3 |
| 3 | Cellophane | 3.0 | 117.2 | 53.95 | in conjunction with the following aqueous-based air-treating material:

| | Parts |
|---|---|
| Water | 95.0 |
| Essential Oil | 1.0 |
| Emulsifier | 1.5 |
| Color | 0.1 |
| Preservative | 0.1 |
| Cellosolve-acetaldehyde blend | 2.3 |

The fragrance release studies were conducted in a membrane cell designed with a small capillary connected to the atmosphere in order to prevent the formation of a partial vacuum due to release of the air-treating material. Pre-swollen membranes were mounted on the cell and the liquid introduced thereafter. The cell was inverted to bring the liquid into contact with the membrane. The loaded cells were then enclosed in a chamber where air was blown through at a predetermined rate. The temperature was maintained at 26° C. and the humidity at 71%. The release rate was determined gravimetrically for a period of time up to about 220 hours, i.e. prior to a complete depletion of the reservoir. As a control, an open cup of air treating material was subjected to the same atmospheric conditions.

The following results were obtained:

| | Air Flow Rate (l/min.) | Release Rate ($10^{-3}$ gm/cm$^2$ hr.) |
|---|---|---|
| Open Cup | $<3 \times 10^{-3}$ | 6.154** |
| Membrane #1 | $<3 \times 10^{-3}$ | 4.118 |
| Membrane #2* | $<3 \times 10^{-3}$ | 2.927 |
| Open Cup | 10 | 12.50** |
| Membrane #1 | 10 | 4.634 |
| Membrane #2* | 10 | 4.146 |
| Membrane #3 | 10 | 7.5 |

*Test conducted in completely sealed cell.
**Initial Rate

The above noted results clearly illustrate the desired reduction in initial release rate exhibited by the systems of this invention. Furthermore, the results indicate that the release through the instant membrane devices is "zero-order" in contrast to the open cup evaporation which exhibits "zero-order" only during the initial stage.

Figure 1:
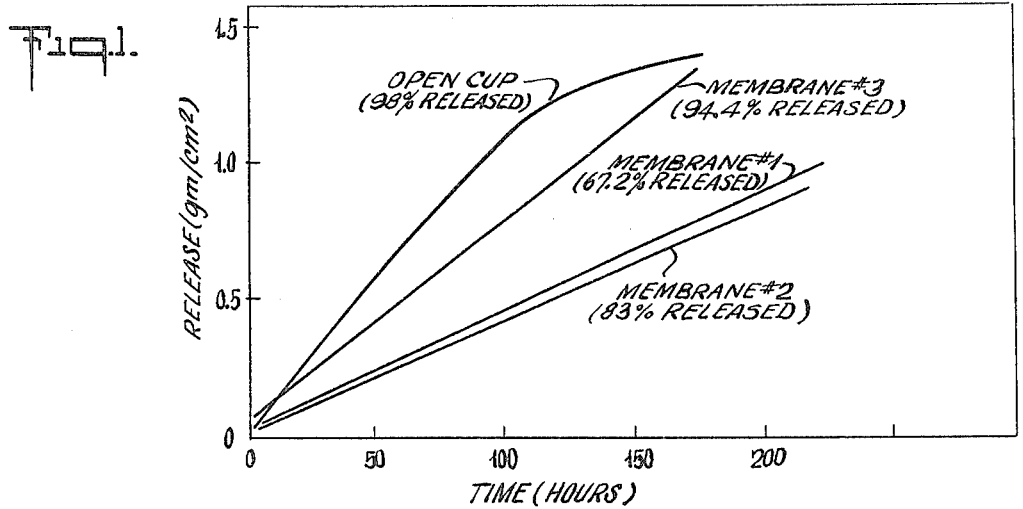
FIGS. 1–3 are graphical depictions of release (gm/cm$^2$) versus time for various membranes of this invention.

The latter result is depicted graphically in FIG. 1 which presents a plot of release (gm/cm$^2$) versus time (hours) at an air flow rate of 10 l/min. Thus, it is seen in FIG. 1 that the systems as reflected in membranes 1-3 provide a substantially controlled, constant rate of release as contrasted with the open cup which exhibits a significantly decreased release with the passage of time.

EXAMPLE II

The procedure of Example I was repeated utilizing the identical aqueous air-treating material and conducting the test procedure at 26° C. and at an average humidity of 59%. Each membrane was tested for at least 200 hours, with several being tested up to 400 hours.

The following tables describe the tested membranes and the test results obtained therewith.

| # | Membrane | Thickness (mils) | Degree of Swelling (%) | Equilibrium H$_2$O content (%) |
|---|---|---|---|---|
| 4 | Crosslinked block polymer of 60% 2-hydroxyethymethacrylate and 40% isocyanate terminated polyether-bisurethane (HEMAC) | 10.0 | 20 | 16.67 |
| 5 | UV cured 70:30 HEMAC | 3.5 | 21 | 17.36 |
| 6 | 80:20 HEMAC | 10.0 | 37 | 27.00 |

| | Air Flow Rate (l/min.) | Release Rate ($10^{-3}$ gm/cm$^2$ hr) |
|---|---|---|
| Open Cup | >12 | 20.7 |
| Membrane #4 | >12 | 1.449 |
| Membrane #5 | >12 | 4.000 |
| Membrane #6 | >12 | 6.418 |

Figure 2:
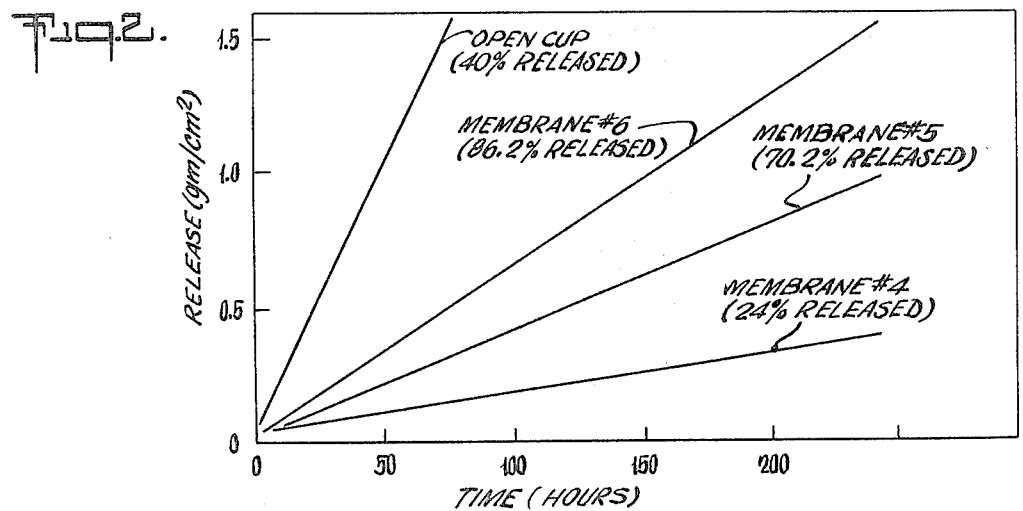

Once again the desired reduction in initial release rate and the release through the membranes in a "zero-order" mechanism were noted. Graphical depictions of the performances of membranes 4-6 are presented in FIG. 2.

EXAMPLE III

Figure 3:
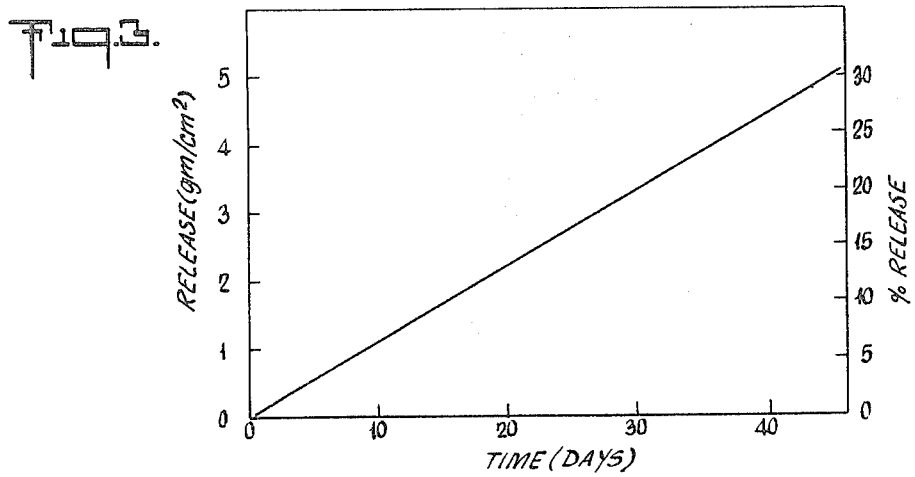

A sealed container was prepared whereby a filter paper dip coated with hydroxyethyl-methacrylate monomer was then cured with ultra-violet radiation directly onto the inside of a front perforated panel, the resulting membrane having a thickness of about 10 mils and an effective area of 12.932 cm$^2$. The aqueous air-treating material of Example I was then introduced into the container by syringe and the pinhole sealed. Release measurements were conducted at room temperature and a humidity of 61% and with substantially no air flow. The unit was run for a period of 44 days and was found to exhibit a constant release rate of 0.1089 gm/cm$^2$day and a total release of 1.4082 gm/day. A graph of the release rate, noted as FIG. 3, revealed a "zero-order" release mechanism.

EXAMPLE IV

The testing apparatus, procedure and aqueous air-treating material of Example I were utilized herein in connection with a microporous polyvinylchloride film (#7) containing an inert, absorptive, inorganic filler, said membrane having a 20 mil thickness, a 150% degree of swelling and a 60% equilibrium water content. The release rate, as determined over a period of 65 hours at room temperature, 61% humidity and in the absence of air flow, was found to be 0.39 gm/cm$^2$day. A plot of the individual readings revealed a "zero-order" release mechanism.

EXAMPLE V

The test procedure of Example I was repeated utilizing the following aqueous air-treating materials and hydrophilic membranes.

|   | Water Content (parts) | Essential Oil Content (parts) | Other Ingredients (parts) |
|---|---|---|---|
| B | 96 | 0.85 | 3.15 emulsifier, color and preservatives |
| C | 96 | 0.85 | 3.15 emulsifier & cellulosic thickener |
| D | 49.5 | 25.0 | 25.5 emulsifier & non-volatile thickener |

| # | Membrane | Thickness (mils) | Degree of Swelling (%) | Equilibrium H$_2$O content (%) |
|---|---|---|---|---|
| 8 | Cuprophan 150 PM | 0.984 | 116.5 | 53.8 |
| 9 | Cuprophan 250 PM | 1.5 | 115.0 | 53.5 |
| 10 | Water-insoluble polyvinyl alcohol (cold H$_2$O insoluble) | 2.6 | 140.0 | 58.3 |

Each test was conducted at two temperatures, at an average humidity of 43% and with an air flow in excess of 12 l/min. Open cup controls were also included in the test procedure.

The results of these tests are presented in the following table:

| Membrane # | Air Treating Agent | Temp. (°C.) | Release Rate (gm/cm$^2$ day) |
|---|---|---|---|
| 8 | B | 23.3 | 1.1520 |
| 8 | B | 35.0 | 3.0648 |
| 8 | C | 23.3 | 1.0047 |
| 8 | C | 35.0 | 2.3460 |
| 8 | D | 35.0 | 0.7093 |
| 9 | B | 23.3 | 1.3440 |
| 9 | B | 35.0 | 2.8464 |
| 10 | B | 23.3 | 1.260 |
| 10 | B | 35.0 | 2.3520 |
| 10 | C | 23.3 | 0.9874 |
| 10 | C | 35.0 | 2.3977 |
| 10 | D | 35.0 | 0.5578 |
| 7 | C | 35.0 | 1.9583 |
| 3 | B | 35.0 | 2.6136 |
| Open Cup | B | 23.3 | 1.8240 |
| Open Cup | B | 35.0 | 3.1872 |
| Open Cup | C | 23.3 | 1.9533 |
| Open Cup | C | 35.0 | 3.4622 |

Once again, the release data for these systems revealed a "zero-order" release rate up to about 80-90% of the total release capacity.

EXAMPLE VI

This example illustrates a further advantage of the instant system in terms of reduced fractionation effects.

Initially, fractionation effects between essential oil components were determined. In this instance, a pre-swollen membrane of water-insoluble polyvinyl alcohol (degree of swelling 140%, equilibrium water content 58.3%, wet thickness 2.6 mils) was mounted on a closed cell and the liquid content introduced thereon. The liquid content was stirred and air at a controlled rate (>11 l./min for membrane cell and >5 l/min for open cup) was blown across the membrane surface to accelerate release. The time course of release was followed gravimetrically. Periodic samples were taken of the liquid remaining in the cell and analyzed by gas-liquid chromatography Comparable analyses were conducted on liquid introduced into an open cup. The essential oil components were categorized as low (0-15 minute retention time), medium (16-34 minute retention time) and high (35-44 minute retention time).

The following formulations were utilized in these tests:

|   | parts E | parts F |
|---|---|---|
| Essential oils | 0.85 | 2.55 |
| Surfactants | 1.34 | 4.02 |
| Dye | 0.50 | 0.50 |
| Preservative | 1.36 | 4.08 |
| Glycerin | — | 1.50 |
| Demineralized water | 95.95 | 87.35 |

The GLC values are presented in the following tables.

Upon combining the results of total release by weight loss as well as the amount released per unit area for the essential oil components, the percentage essential oil released as well as the percentage released for the essential oil components is determined and are also presented in the following tables. In each instance, the open cup area was 5.1875 cm$^2$ and the membrane area was 23.7583 cm$^2$.

Formulation E
Control (open cup)

| Time (hr) | GLC Analysis Low (%) | Med (%) | High (%) | % Release Low (%) | Med (%) | High (%) | % Oil Release |
|---|---|---|---|---|---|---|---|
| 0 | 17.9 | 71.4 | 10.6 | 0 | 0 | 0 | 0 |
| 3.92 | 17.6 | 71.2 | 11.0 | 9.59 | 8.29 | 4.55 | 8.05 |
| 23.42 | 15.5 | 69.9 | 14.6 | 37.12 | 28.89 | — | 27.39 |
| 48.75 | 9.9 | 68.9 | 21.2 | 75.03 | 56.44 | 9.69 | 54.87 |
| 71.67 | 5.8 | 67.1 | 27.1 | 89.95 | 70.89 | 20.79 | 69.43 |
| 95.26 | 3.4 | 67.0 | 29.6 | 95.34 | 76.97 | 31.48 | 75.46 |

Membrane Cell

| Time (hr) | GLC Analysis Low (%) | Med (%) | High (%) | % Release Low (%) | Med (%) | High (%) | % Oil Release |
|---|---|---|---|---|---|---|---|
| 0 | 17.9 | 71.4 | 10.6 | 0 | 0 | 0 | 0 |
| 4.97 | 18.1 | 71.3 | 10.5 | 2.46 | 3.66 | 4.37 | 3.52 |
| 24.7 | 18.4 | 70.8 | 10.8 | 2.90 | 6.31 | 3.70 | 5.52 |
| 49.92 | 19.5 | 69.1 | 11.4 | 6.43 | 16.88 | 7.62 | 14.11 |
| 74.42 | 19.2 | 69.5 | 11.3 | 12.81 | 20.85 | 13.27 | 18.69 |
| 97.85 | 20.2 | 71.1 | 8.7 | 13.04 | 22.49 | 36.12 | 22.15 |

Formulation F
Control (open cup)

| Time (hr) | GLC Analysis Low (%) | Med (%) | High (%) | % Release** Low (%) | Med (%) | High (%) | % Oil Release**** |
|---|---|---|---|---|---|---|---|
| 0 | 19.81 | 71.15 | 9.03 | 0 | 0 | 0 | 0 |
| 2.67 | 19.43 | 71.13 | 9.44 | 6.19 | 4.35 | 0.18 | 4.32 |
| 22.7 | 15.09 | 73.43 | 11.48 | 46.01 | 26.89 | 10.05 | 29.16 |
| 47.67 | 0.20 | 85.76 | 14.23 | 99.54 | 45.24 | 28.40 | 54.57 |
| 70.92 | 0.20 | 85.00 | 14.80 | 99.60 | 52.10 | 34.39 | 59.91 |

Membrane Cell

| Time | GLC Analysis Low | Med | High | % Release* Low | Med | High | % Oil |
|---|---|---|---|---|---|---|---|

| (hr) | (%) | (%) | (%) | (%) | (%) | (%) | Release*** |
|---|---|---|---|---|---|---|---|
| 0 | 19.81 | 71.15 | 9.03 | 0 | 0 | 0 | 0 |
| 3.85 | 20.29 | 69.91 | 9.80 | 6.16 | 9.97 | 0.33 | 8.38 |
| 24.0 | 20.95 | 70.38 | 8.67 | 13.77 | 19.34 | 15.82 | 18.47 |
| 49.09 | 22.37 | 68.61 | 9.01 | 44.81 | 52.87 | 51.30 | 51.13 |
| 73.29 | 24.71 | 65.25 | 10.04 | 80.60 | 85.73 | 82.72 | 84.44 |

*Data depicted in FIG. 4.
**Data depicted in FIG. 5.
***Data depicted in FIG. 6.
****Data depicted in FIG. 7

The data presented hereinabove thus clearly reveals the substantial reduction in essential oil and essential oilwater fractionation with the instant system. Referring specifically to the graphs (FIGS. 4–7) for formulation F,
linear release characteristics are exhibited. The percentage essential oil release follows closely with the percentage total release (FIG. 6) indicating no fractionation between water and essential oil as compared to the open cup evaporation where fractionation does occur (FIG. 7). In other words, the essential oil concentration in the PVA membrane system remained pretty much the same during the whole course of release study. FIGS. 4 and 5 further show that there is practically no fractionation among components of the essential oil in the PVA membrane system as compared to that in the open cup control where fractionation prevails.

Corresponding data were developed for formulation F utilizing the identical test procedure except for the elimination of the air blown across the membrane surface. Thus, stagnant conditions were achieved. The following results were obtained.

| | Membrane Cell GLC Analysis | | | Membrane Cell (% Release) | | | |
|---|---|---|---|---|---|---|---|
| Time (hr) | Low (%) | Med (%) | High (%) | Low (%) | Med (%) | High (%) | % Oil Release |
| 0 | 29.50 | 56.97 | 13.53 | 0 | 0 | 0 | 0 |
| 76.50 | 35.84 | 48.90 | 15.26 | — | — | — | 7.60 |
| 167.67 | 34.64 | 50.54 | 14.81 | 15.6 | 36.3 | 21.4 | 28.16 |
| 243.75 | 32.80 | 55.74 | 11.47 | 56.2 | 61.5 | 45.5 | 60.64 |
| 313.84 | 43.39 | 39.73 | 16.97 | 66.8 | 78.2 | 60.9 | 68.8 |

It is seen that comparable elimination of fractionation is also achieved under stagnant conditions.

Furthermore, minimum fractionation was also observed when evergreen oil and honeysuckle oil, absent surfactant concentrations, were subjected to similar test procedures.

Summarizing, it is seen that this invention provides a unique system for the controlled release of air-treating materials. Variations may be made in proportions, procedures and materials without departing from the scope of the invention as defined by the following claims.

What is claimed is:

1. A dispensing system for volatile air-treating materials comprising a closed reservoir, a hydrophilic membrane having an equilibrium water content of at least about 15% forming at least a portion of the wall surface of said reservoir and being in contact with the atmosphere, and a volatile air-treating material present in aqueous medium contained in said reservoir in contact with said hydrophilic membrane; said system providing uniform release of both said water and said volatile air-treating material such that said reservoir is substantially devoid of both components at the conclusion of the release period, and substantially minimizing the fractionation among any essential oils present in said air-treating material and between the water and said essential oils.

2. The dispensing system of claim 1, wherein said hydrophilic membrane is selected from the group consisting of cellophane; Cuprophan; high molecular weight, fully hydrolyzed polyvinyl alcohol; crosslinked polyvinyl alcohol; hydrogels; polyvinyl chloride containing inert, absorptive filler; cellulose triacetate; copolyether polycarbonate; polyethylene glycol-polyethylene terephthalate copolymer; and hydrophilic polyurethane.

3. The dispensing system of claim 1, wherein said equilibrium water content is at least about 30%.

4. The dispensing system of claim 1, wherein said aqueous medium is a water-solvent mixture selected from the group consisting of water-alcohol, water-glycol, water-ketone and water-aldehyde.

5. The dispensing system of claim 2, wherein said hydrophilic membrane is cold water-insoluble polyvinyl alcohol.

6. The dispensing system of claim 1, wherein said reservoir is a rigid container having means for vacuum relief.

7. The dispensing system of claim 1, wherein said reservoir is a flexible container.

8. The dispensing system of claim 1, wherein said hydrophilic membrane is supported on a macroporous substrate.

9. The dispensing system of claim 1, wherein said air-treating material is present in an oil-in-water emulsion.

10. A method for the controlled, uniform, substantially constant release of volatile air-treating materials into the atomsphere comprising placing an aqueous system containing said volatile air-treating material into a closed reservoir having as at least a portion of the wall surface thereof a hydrophilic membrane with an equilibrium water content of at least about 15%, said aqueous system contacting said membrane; swelling said membrane; and allowing said air-treating material to diffuse through said membrane and be released into the atmosphere; said aqueous phase also being transmitted through said membrane such that said reservoir is substantially empty at the conclusion of the release period.

11. The method of claim 10, wherein said hydrophilic membrane is selected from the group consisting of polyvinyl alcohol; crosslinked polyvinyl alcohol; hydrogels; polyvinyl chloride containing inert, absorptive filler; cellulose triacetate; copolyether polycarbonate; polyethylene glycol-polyethylene terephthalate copolymer; and hydrophilic polyurethane.

12. The method of claim 10, wherein said aqueous medium is a water-solvent mixture selected from the group consisting of water-alcohol, water-glycol, water-ketone and water-aldehyde.

13. The method of claim 11, wherein said hydrophilic membrane is cold water-insoluble polyvinyl alcohol.

* * * * *